United States Patent [19]
Johnson

[11] Patent Number: 5,633,016
[45] Date of Patent: May 27, 1997

[54] COMBINATION CHEMOTHERAPY

[75] Inventor: Randall K. Johnson, Ardmore, Pa.

[73] Assignee: SmithKline Beecham Corporation, Philadelphia, Pa.

[21] Appl. No.: 434,897

[22] Filed: May 1, 1995

Related U.S. Application Data

[63] Continuation of Ser. No. 240,648, filed as PCT/US92/09864 Nov. 13, 1992, abandoned.

[51] Int. Cl.$^6$ .......................... A61K 33/24; A61K 31/44
[52] U.S. Cl. .............................. 424/649; 514/283
[58] Field of Search ................. 514/283; 424/649

[56] References Cited

U.S. PATENT DOCUMENTS 5,004,758 4/1991 Boehm et al. ................... 514/283

FOREIGN PATENT DOCUMENTS 92925253 3/1996 European Pat. Off. .

OTHER PUBLICATIONS

Burris et al., "Topoisomerase I Inhibitors, An Overview of the Camptothecin Analogs", (1994), Hematol. Oncol. Clin. North Am., vol. 8, No. 2, pp. 333–355.
Kano, et al., "Effects of CPT–11 in Combination With Other Anti–Cancer Agents in Culture", (1992), Int. J. Cancer, vol. 50, No. 4, pp. 604–610.
Furuta et al., "Combination Therapy of CPT–11, a Camptothecin Derivative With Various Antitumor Drugs Against L 1210 Leukemia", (1991), STN International, Karlsruhe, 18(3), pp. 393–402 Abstract Only.
Drewinko, et al., "Combination Chemotherapy In Vitro with Cis–dichlorodiammineplatinum(II)", (1976), Cancer Treat. Rep., vol. 60, No. 11, pp. 1619–1625.
Drewinko, et al., "Action of Cis–dichlorodiammineplatinum(II) (NCS–119875) at the Cellular Level", (1975), Cancer Chemother. Rep., vol. 59, No. 3, pp. 665–673.

Bin et al., *Advances in Chinese Medicinal Materials Research*, edited by Chang et al., 1985 World Scientific Publ. Co., Singapore, 377–389.
Tung et al., *Chinese Medical Journal*, 92(1), 57–60 (1979).
Moertal et al., *Cancer Chemotherapy Reports Part 1*, 56(1), 95–101 Feb. 1972.
Gottlieb et al., *Cancer Chemotherapy Reports Part 1*, 56(1), 103–105 Feb. 1972.
Muggia et al., *Cancer Chemotherapy Reports Part 1*, 56(4), 515–521, Aug. 1972.
Gottlieb et al., *Cancer Chemotherapy Reports Part 1*, 54(6), 461–470, Dec. 1970.
Wall et al., Abstract 336, *Proceedings of ASCO*, vol. 9 (Mar. 1990).
Kuhn et al., Abstract 269, *Proceedings of ASCO*, vol. 9 (Mar. 1990).
Abstract 00011628, Pharmaprojects, PJB Publications Ltd., Richmond, Surrey UK, Jun. 26, 1990.
Carter et al., *Chemotherapy of Cancer*, 2nd Ed., 107–108 (Aug. 13, 1981).
Carter et al, Chemotherapy of Cancer, 2nd Ed, John Wiley & Sons, N.Y., N.Y., pp. 107 and 108 (1981).

*Primary Examiner*—Jerome D. Goldberg
*Attorney, Agent, or Firm*—Yuriy P. Stercho; Stephen Venetianer; Edward T. Lentz

[57] ABSTRACT

A pharmaceutical composition comprising a compound of the camptothecin analog class and a platinum coordination compound and a pharmaceutically acceptable carrier or diluent; a method of inhibiting the growth of tumor cells in a human afflicted therewith which comprises administering to such human an effective tumor cell growth inhibiting amount of such pharmaceutical composition; and a method of inhibiting the growth of tumor cells in a human afflicated therewith which comprises administering to such human an effective tumor cell growth inhibiting amount of the combination of a compound of the camptothecin analog class and a platinum coordination compound.

8 Claims, No Drawings

COMBINATION CHEMOTHERAPY

This is a continuation of application Ser. No. 08/240,648, filed May 13, 1994, abandoned, and PCT/US92/09864 filed 11/13/92.

CROSS-REFERENCES

The present application claims the benefit of the filing date of International Application Number PCT/US92/09864, having an International Filing date of Nov. 13, 1992, which application claims the benefit of the filing date of U.S. Ser. No. 07/793,041, now abandoned.

BACKGROUND OF THE INVENTION

This invention relates to a pharmaceutical composition comprising a compound of the camptothecin analog class and a platinum coordination compound and a pharmaceutically acceptable carrier or diluent. This invention also relates to a method of inhibiting the growth of tumor cells in a human afflicted therewith which comprises administering to such human an effective tumor cell growth inhibiting amount of such pharmaceutical composition. This invention also relates to a method of inhibiting the growth of tumor cells in a human afflicated therewith which comprises administering to such human an effective tumor cell growth inhibiting amount of the combination of a compound of the camptothecin analog class and a platinum coordination compound.

Cisplatin, or cis-dichlorodiammineplatinum II, has been used successfully for many years as a chemotherapeutic agent in the treatment of various human solid malignant tumors. More recently, other diamino-platinum complexes have also shown efficacy as chemotherapeutic agents in the treatment of various human solid malignant tumors. Such diamino-platinum complexes include, but are not limited to, spiroplatinum and carboplatinum.

Although cisplatin and other diamino-platinum complexes have been widely used as chemotherapeutic agents in humans, they are not therapeutically effective in all patients or agaisnt all types of solid tumors. Moreover, such compounds have to be delivered at high dosage levels which can lead to toxicity problems such as kidney damage.

Topotecan and every compound of the camptothecin analog class are each a specific inhibitor of DNA topoisomerase I. Topoisomerases are enzymes that are capable of altering DNA topology in eukaryotic cells. They are critical for important cellular functions and cell proliferation. There are two classes of topoisomerases in eukaryotic cells, type I and type II. Topoisomerase I is a monomeric enzyme of approximately 100,000 molecular weight. The enzyme binds to DNA and introduces a transient single-strand break, unwinds the double helix (or allows it to unwind), and subsequently reseals the break before dissociating from the DNA strand. Topotecan has recently shown clinical efficacy as the sole chemotherapeutic agent in the treatment of humans afflicated with ovarian cancer, esophageal cancer or non-small cell lung carcinoma.

There is a need for increasing the efficacy of the tumor cell growth inhibiting activity of cisplatin and other diamino-platinum complexes and/or providing a means for the use of lower dosages of cisplatin and other diamino-platinum complexes to reduce the potential of adverse toxic side effects to the patient.

The pharmaceutical composition and methods of this invention fill such a need. It has now been found that a compound of the camptothecin analog class, such as topotecan, demonstrates a therapeutic synergism when administered with a platinum coordination compound, such as cisplatin, thereby potentially increasing the tumor cell growth inhibiting activity of such platinum coordination compound. It has also now been found that such synergism likely results in a need for lower doses of such platinum coordination compound when administered with a compound of the camptothecin analog class as compared to the doses required when such platinum coordination compound is administered without a compound of the camptothecin analog class.

SUMMARY OF THE INVENTION

This invention relates to a pharmaceutical composition comprising a compound of the camptothecin analog class and a platinum coordination compound and a pharmaceutically acceptable carrier or diluent; a method of inhibiting the growth of tumor cells in a human afflicted therewith which comprises administering to such human an effective tumor cell growth inhibiting amount of such pharmaceutical composition; and a method of inhibiting the growth of tumor cells in a human afflicated therewith which comprises administering to such human an effective tumor cell growth inhibiting amount of the combination of a compound of the camptothecin analog class and a platinum coordination compound.

DETAILED DESCRIPTION OF THE INVENTION

Camptothecin is a water-insoluble, cytotoxic alkaloid produced by *Camptotheca accuminata* trees indigenous to China and *Nothapodytes foetida* trees indigenous to India. Camptothecin exhibits tumor cell growth inhibiting activity against those tumor cells which are sensitive to it. Camptothecin has the following chemical structure:

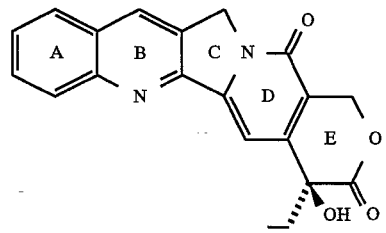

It is recognized that due to the asymmetric carbon atom in the E ring of camptothecin, optical isomers will exist. The S-isomer is the preferred isomer for tumor cell growth inhibiting activity.

By the term "a compound of the camptothecin analog class" is meant any tumor cell growth inhibiting compound which is structurally related to camptothecin. Compounds of the camptothecin analog class include, but are not limited to, topotecan, irinotecan and 9-aminocamptothecin. Such compounds also include, but are not limited to, any tumor cell growth inhibiting camptothecin analog claimed or described in:

U.S. Pat. No. 5,004,758, issued on Apr. 2, 1991 and European Patent Application Number 88311366.4, published on Jun. 21, 1989 as Publication Number EP 0 321 122, U.S. Pat. No. 4,604,463, issued on Aug. 5, 1986 and European Patent Application Publication Number EP 0 137 145, published on Apr. 17, 1985;

U.S. Pat. No. 4,473,692, issued on Sep. 25, 1984 and European Patent Application Publication Number EP 0 074 256, published on Mar. 16, 1983;

U.S. Pat. No. 4,545,880, issued on Oct. 8, 1985 and European Patent Application Publication Number EP 0 074 256, published on Mar. 16, 1983;

European Patent Application Publication Number EP 0 088 642, published on Sep. 14, 1983;

Wani et al., *J. Med. Chem.*, 29, 2358–2363 (1986);

Nitta et al., Proc. 14th International Congr. Chemotherapy, Kyoto, 1985, Tokyo Press, Anticancer Section 1, p. 28–30, especially a compound called CPT- 11. CPT-11 is a camptothecin analog with a 4-(piperidino)-piperidine side chain joined through a carbamate linkage at C-10 of 10 -hydroxy-7-ethyl camptothecin. CPT-11 is currently undergoing human clinical trials and is also referred to as irinotecan;

Wani et al., *J. Med. Chem.*, 23, 554 (1980);

Wani et. al., *J. Med Chem*, 30, 1774 (1987);

U.S. Pat. No. 4,342,776, issued on Aug. 3, 1982;

U.S. patent application Ser. No. 581,916, filed on Sep. 13, 1990 and European Patent Application Publication Number EP 418 099, published on Mar. 20, 1991;

U.S. Pat. No. 4,513,138, issued on Apr. 23, 1985 and European Patent Application Publication Number EP 0 074 770, published on Mar. 23, 1983;

U.S. Pat. No. 4,399,276, issued on Aug. 16, 1983 and European Patent Application Publication Number 0 056 692, published on Jul. 28, 1982; the entire disclosure of each of which is hereby incorporated by reference. All of the above-listed compounds of the camptothecin analog class are available commercially and/or can be prepared by conventional techniques including those described in the above-listed references.

Preferably the compound of the camptothecin analog class is selected from the group consisting of topotecan, irinotecan and 9-aminocamptothecin. Preferably the compound of the camptothecin analog class is water soluble.

Also preferably the compound of the camptothecin analog class is selected from the tumor cell growth inhibiting camptothecin analogs claimed in U.S. Pat. No. 5,004,758, issued on Apr. 2, 1991 and European Patent Application Number 88311366.4, published on Jun. 21, 1989 as Publication Number EP 0 321 122. The preparation of any such compound of the camptothecin analog class (including pharmaceutically acceptable salts, hydrates and solvates thereof) as well as the preparation of oral and parenteral pharmaceutical compositions comprising such a compound of the camptothecin analog class and an inert, pharmaceutically acceptable carrier or diluent, is extensively described in U.S. Pat. No. 5,004,758, issued on Apr. 2, 1991 and European Patent Application Number 88311366.4, published on Jun. 21, 1989 as Publication Number EP 0 321 122.

Topotecan is the most preferred compound of the camptothecin analog class. By the term "topotecan" as used herein is meant (S)-9-dimethylaminomethyl-10-hydroxycamptothecin and any pharmaceutically acceptable salt, hydrate or solvate thereof. Topotecan's chemical name is (S)-10[(dimethylamino)methyl]-4-ethyl-4,9-dihydroxy-1H-pyrano[3',4':6,7]indolizino[1,2-b]quinolone-3,14(4H,12H)-dione.

Topotecan is water-soluble by virtue of the presence of the basic side-chain at position 9 which forms salts with acids. Preferred salt forms of topotecan include the hydrochloride salt, acetate salt and methanesulfonic acid salt. An alkali metal salt form of the carboxylate formed on alkaline hydrolysis of the E-ring lactone of topotecan would also yield a soluble salt, such as the sodium salt.

The preparation of topotecan (including pharmaceutically acceptable salts, hydrates and solvates thereof) as well as the preparation of oral and parenteral pharmaceutical compositions comprising topotecan and an inert, pharmaceutically acceptable carrier or diluent, is extensively described in U.S. Pat. No. 5,004,758, issued on Apr. 2, 1991 and European Patent Application Number 88311366.4, published on Jun. 21, 1989 as Publication Number EP 0 321 122.

By the term "platinum coordination compound" is meant any tumor cell growth inhibiting platinum coordination compound which provides the platinum in the form of an ion. Preferred platinum coordination compounds include cisplatin; cis-diamminediaquoplatinum (II)-ion; chloro (diethylenetriamine)-platinum(II) chloride; dichloro (ethylenediamine)-platinum(II); diammine(1,1-cyclobutanedicarboxylato) platinum(II) (Carboplatin); Spiroplatin; Iproplatin; diammine(2-ethylmalonato)-platinum(II); ethylenediaminemalonatoplatinum(II); aqua (1,2-diaminodyclohexane)-sulfatoplatinum(II); (1,2-diaminocyclohexane)malonatoplatinum(II); (4-caroxyphthalato)(1,2-diaminocyclohexane)platinum(II); (1,2-diaminocyclohexane)-(isocitrato)platinum(II); (1,2-diaminocyclohexane)cis(pyruvato)platinum(II); and (1,2-diaminocyclohexane)oxalatoplatinum(II); Ormaplatin; and Tetraplatin.

Cisplatin is the most preferred platinum coordination compound. By the term "cisplatin" is meant cis-dichlorodiammine platinum (II). Cisplatin is commercially available. For example, cisplatin is available under the name Platinol® from Bristol Myers-Squibb Corporation as a powder for constitution with water, sterile saline or other suitable vehicle. Other platinum coordination compounds named herein are known and are available commercially and/or can be prepared by conventional techniques.

This invention relates to a method of inhibiting the growth of tumor cells in a human afflicted therewith which comprises administering to such human an effective tumor cell growth inhibiting amount of a compound of the camptothecin analog class and a platinum coordination compound. One preferred aspect of this invention relates to a method of inhibiting the growth of tumor cells in a human afflicted therewith which comprises administering to such human an effective tumor cell growth inhibiting amount of topotecan and cisplatin.

By the term "inhibiting the growth of tumor cells" as used herein is meant the inhibition of the growth of tumor cells which are sensitive to the method of the subject invention, i.e., therapy involving the administration of an effective amount of the combination of a compound of the camptothecin class, such as topotecan, and a platinum coordination compound, such as cisplatin to a human afflicted therewith. Preferably such treatment also leads to the regression of tumor growth, i.e., the decease in size of a measurable tumor. Most preferably, such treatment leads to the complete regression of the tumor.

By the term "administering" or "administered" as used herein is meant parenteral and/or oral administration. By "parenteral" is meant intravenous, subcutaneous and intra-muscular administration. In the method of the subject invention, the compound of the camptothecin class may be administered simultaneously with the platinum coordination compound, or the compounds may be administered sequentially, in either order. It will be appreciated that the actual preferred method and order of administration will vary according to, inter alia, the particular formulation of a compound of the camptothecin analog class (such as topotecan) being utilized, the particular formulation of a platinum coordination compound (such as cisplatin) being utilized, the particular tumor cells being treated, and the particular host being treated. The optimal method and order of administration of the compound of the camptothecin analog class and the platinum coordination compound for a given set of conditions can be ascertained by those skilled in the art using conventional techniques and in view of the information set out herein.

By the term "effective tumor cell growth inhibiting amount of a compound of the camptothecin analog class and a platinum coordination compound" as used herein is meant a course of therapy which will result in inhibiting the growth of tumor cells sensitive to such therapy in a human afflicted therewith. Preferably, such course of therapy will result in the administration of a lower dose of a platinum coordination compound than is required when such compound is administered as the sole chemotherapeutic agent; and/or will result in enhancement of the tumor cell growth inhibiting efficacy of the compound of the camptothecin class and/or the platinum coordination compound as compared to when such compound is administered as the sole chemotherapeutic agent. It will be appreciated that the actual preferred course of therapy will vary according to, inter alia, the mode of administration of the compound of the camptothecin analog class, the particular formulation of a compound of the camptothecin analog class (such as topotecan) being utilized, the particular formulation of a platinum coordination compound (such as Lisplatin) being utilized, the mode of administration of the platinum coordination compound, the particular tumor cells being treated and the particular host being treated. The optimal course of therapy for a given set of conditions can be ascertained by those skilled in the art using conventional course of therapy determination tests and in view of the information set out herein.

In the method of the subject invention, the platinum coordination compound can be administered in the same manner as in prior clinical practice. More specifically, slow intravenous infusion is the method of choice for cisplatin. For promoting diuresis when using cisplatin or other potentially nephrotoxic platinum coordination compounds, the incorporation of mannitol in a dextrose/saline solution is the preferred carrier. The protocol can also include prehydration of the patient by administration of a dextrose/saline solution before the cisplatin. In the method of the subject invention, the dose schedule of the platinum coordination compound may be on the basis of from about 1 to about 500 mg per square meter ($mg/m^2$) of body surface area per course of treatment. For the method of the subject invention utilizing cisplatin and topotecan, the preferred dosage of cisplatin would be a single dose of from about 30 to about 100 $mg/m^2$ of cisplatin at the end of a one to five consecutive day course of treatment with topotecan. Infusions of the platinum coordination compound may be given one to two times weekly, and the weekly treatments repeated several times unless renal toxicity, neurotoxicity or other side effects provide a contraindication. Other conventional practices may be employed in conjunction with the administration of cisplatin or other compounds of the platinum coordination complex class.

In the method of the subject invention, for parenteral administration of a compound the camptothecin analog class, the course of therapy generally employed is from about 0.1 to about 300.0 $mg/m^2$ of body surface area per day for about one to about five consecutive days. More preferably, the course of therapy employed is from about 0.1 to about 100 $mg/m^2$ of body surface area per day for about five consecutive days. Most preferably, the course of therapy employed for topotecan is from about 1.0 to about 2.0 $mg/m^2$ of body surface area per day for about five consecutive days. Preferably, the course of therapy is repeated at least once at about a seven day to about a twenty-eight day interval (from the date of initiation of therapy) depending upon the initial dosing schedule and the patient's recovery of normal tissues. Most preferably, the course of therapy continues to be repeated based on tumor response.

Preferably, the parenteral administration of a compound of the camptothecin analog class will be by short (e.g., 30 minute) or prolonged (e.g., 24 hour) intravenous infusion. More preferably, the a compound the camptothecin analog class will be administered by a 30 minute intravenous infusion.

At this time, in the method of the subject invention, it is believed that the most preferred course of parenteral therapy with topotecan to be employed for a previously non-treated or lightly pretreated patient is an initial course of therapy of 1.5 $mg/m^2$ of body surface area per day administered by short intravenous infusion for five consecutive days. When the patient has recovered sufficiently from the drug-related effects of this initial course, an additional course of therapy of at least 1.5 $mg/m^2$ of body surface area per day is administered by short intravenous infusion for five consecutive days, to be repeated based on tumor response.

At this time, in the method of the subject invention, it is believed that the most preferred course of parenteral therapy with topotecan to be employed for a heavily pretreated patient is an initial course of therapy of 1.0 $mg/m^2$ of body surface area per day administered by short intravenous infusion for five consecutive days. When the patient has recovered sufficiently from the drug-related effects of this initial course, an additional come of therapy of at least 1.0 mg of topotecan/$m^2$ of body surface area per day is administered by short intravenous infusion for five consecutive days, such course of therapy to be repeated based on tumor response.

In the method of the subject invention, for oral administration of a compound the camptothecin analog class, the come of therapy generally employed is from about 1.0 to about 500.0 $mg/m^2$ of body surface area per day for about one to five consecutive days. More preferably, the course of therapy employed for topotecan is from about 1.5 to about 5.0 $mg/m^2$ of body surface area per day for about five consecutive days. Preferably, the course of therapy is repeated at least once at about a seven day to about a twenty-eight day interval (from the date of initiation of therapy) depending upon the initial dosing schedule and the patient's recovery of normal tissues. Most preferably, the course of therapy continues to be repeated based on tumor response.

The pharmaceutical composition of this invention contains both a compound of the camptothecin analog class and a platinum coordination compound as well as a pharmaceutically acceptable carrier or diluent. The appropriate pharmaceutically acceptable carriers and diluents to be utilized in the composition of the invention are well known to those skill in the art of formulating compounds into pharmaceutical compositions. The pharmaceutical composition of the invention will be in a form suitable, for parenteral administration. Such composition may be formulated for intravenous infusion or injection in numerous ways well known to those skilled in the art with pharmaceutically acceptable carriers. Preferably, such pharmaceutical composition is in the form of a freeze-dried mixture of the two active ingredients in a unit dosage form, prepared by conventional techniques, which can be reconstituted with water or other suitable infusion liquid at the time of administration.

It will be recognized by one of skill in the art that the content of the active ingredients in the pharmaceutical composition of this invention may vary quite widely depending upon numerous factors, such as, the desired dosage and the pharmaceutically acceptable carrier being employed. For administration, in the pharmaceutical composition of the invention, the content of the compound of the camptothecin analog class will usually be 10:1 to 1000:1 by weight, with respect to the content of the platinum coordination compound present in the composition. Preferably, the pharmaceutical composition of the invention will contain from 5 mg to 500 mg of the platinum coordination complex class compound, and from 100 mg to 10,000 mg of the compound of the camptothecin analog class. Mannitol and/or sodium chloride may preferably be included in amounts conventional for cisplatin preparations. Physiological pH of injectables or infusion drug combinations will be established by inclusion of buffering agents as is known in the pharmaceutical formulation art.

Clinical Pharmaceutical Information

Topotecan is currently undergoing Phase I clinical investigation. The following pharmaceutical information is being supplied to the clinicians:

How supplied - As a vial containing 5 mg (of the base) with 100 mg mannitol. The pH is adjusted to 3.0 with HCl/NaOH. Lyophilized powder is light yellow in color. Intact vials should be stored under refrigeration (2–8 degrees Centigrade).

Solution Preparation - When the 5 mg vial is reconstituted with 2 ml of Sterile Water for Injection, USP, each ml will contain 2.5 mg of topotecan as the base and 50 mg of mannitol, USP. Topotecan must not be diluted or mixed with buffered solutions because of solubility and stability considerations.

Stability - Shelf life surveillance of the intact vials is ongoing. Because the single-use lyophilized dosage form contains no antibacterial preservatives, it is advised that the reconstituted solution be discarded eight hours after initial entry into the vial. Further dilutions of the reconstituted solution to concentrations of 0.02 mg/ml and 0.1 mg. ml in 5% Dextrose Injection, USP, ("D5W") or 0.9% Sodium Chloride Injection, USP, ("NS") in plastic bags stored at room temperature yielded the following stability results:

| Percentage of Initial Topotecan Remaining in Solution | | | |
|---|---|---|---|
| | | Concentration | |
| Diluent | Time (hrs) | 0.02 mg/ml | 0.1 mg/ml |
| D5W | 0 | 100.00 | 100.00 |
| | 6 | 99.29 | 99.68 |
| | 24 | 102.30 | 98.16 |
| | 48 | 101.98 | 97.91 |
| NS | 0 | 100.00 | 100.00 |
| | 6 | 98.58 | 97.71 |
| | 24 | 96.01 | 98.30 |
| | 48 | 102.03 | 98.35 |

Topotecan diluted in saline (10 ug/ml or 500 ug/ml) or dextrose (6.7 ug/ml or 330 ug/ml) is stable in a hang-bag for 24 hours with at least 95% recovery.

Treatment dose - The treatment dose is to be diluted in a final volume of 150 ml of Sodium Chloride Injection, USP (without preservatives) and administered over a 30 minute period. The treatment dose is to be kept under refrigeration and protected from light and it is to be used within 24 hours.

Tumor cell growth inhibiting activity

The efficacy of the combination of topotecan and cisplatin in several widely utilized transplantable mouse tumor models was assessed. The results of such assayed showed that the combination of topotecan and cisplatin demonstrated therapeutic synergism (i.e., an effect greater than can be achieved with either drug used individually at its maximally tolerated dose) in the following mouse tumor models:

Mice bearing advanced systemic intravenously implanted L1210 leukemia were treated with one intraperitoneal (ip) bolus of the combination on day 3 after implantation;

Mice bearing advanced pulmonary intravenously implanted Lewis Lung carcinoma treated with ip bolus of the combination on days 7 and 14 after implantation;

Mice bearing advanced subcutaneously implanted B16 melanoma treated with intravenous (iv) bolus of the combination on days 11, 15 and 19 after implantation. No therapeutic synergism was observed when mice bearing established subcutaneously implanted mammary adenocarcinoma 16/C were treated with ip bolus of the combination on days 8 and 15 after implantation.

What is claimed is:

1. A method of inhibiting the growth of tumor cells sensitive to a synergistic effective amount of topotecan in combination with a synergistic effective amount of cisplatin, in a human afflicted therewith, which comprises administering to such human an effective amount of topotecan in combination with an effective amount of cisplatin sufficient to achieve synergistic tumor growth inhibition.

2. A method according to claim 1 wherein a single dose of about 30 to about 100 mg/m$^2$ of body surface area of cisplatin is administered parenterally at the end of a consecutive one to five day course of treatment with topotecan.

3. A method according to claim 1 wherein said cisplatin is administered by slow intravenous infusion.

4. A method according to claim 1 wherein said topotecan is administered by intravenous infusion.

5. A method according to claim 1 wherein topotecan is administered orally in a course of therapy employing about 1.5 to about 5.0 mg/m$^2$ of body surface area per day for about five consecutive days.

6. A method according to claim 1 wherein topotecan is administered parenterally in a course of therapy employing about 0.1 to about 300.0 mg/m$^2$ of body surface area per day for about one to about five consecutive days.

7. A method according to claim 6 wherein topotecan is administered parenterally in a course of therapy employing about 1.0 to about 2.0 mg/m$^2$ of body surface area per day for about five consecutive days.

8. A pharmaceutical composition comprising a synergistic effective amount of topotecan, a synergistic effective amount of cisplatin, and a pharmaceutically acceptable carrier or diluent.

* * * * *